(12) United States Patent
Berberich

(10) Patent No.: US 9,848,891 B2
(45) Date of Patent: Dec. 26, 2017

(54) TOOL AND METHOD FOR GENERATING AN UNDERCUT IN A BONE

(71) Applicant: Karl Storz SE & Co. KG, Tuttlingen (DE)

(72) Inventor: Sascha Berberich, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 91 days.

(21) Appl. No.: 14/661,942

(22) Filed: Mar. 18, 2015

(65) Prior Publication Data

US 2015/0265287 A1    Sep. 24, 2015

(30) Foreign Application Priority Data

Mar. 18, 2014  (DE) .................. 10 2014 003 721
Feb. 20, 2015  (EP) ..................... 15000497

(51) Int. Cl.
*A61B 17/16*    (2006.01)

(52) U.S. Cl.
CPC ...... *A61B 17/1633* (2013.01); *A61B 17/1615* (2013.01); *A61B 17/1617* (2013.01); *A61B 17/1637* (2013.01)

(58) Field of Classification Search
CPC .................................................. A61B 17/1633
See application file for complete search history.

(56) References Cited

U.S. PATENT DOCUMENTS

| 4,446,934 A * | 5/1984 | Muller ................ B23B 51/0045 175/286 |
| 4,635,737 A * | 1/1987 | Miyanaga ........... B23B 51/0045 175/284 |
| 4,998,981 A * | 3/1991 | Miyanaga ........... B23B 51/0045 175/202 |
| 5,004,421 A * | 4/1991 | Lazarof ................ A61C 8/0033 433/173 |
| 5,735,650 A * | 4/1998 | Miyanaga ........... B23B 51/0045 175/286 |
| 5,810,523 A * | 9/1998 | Miyanaga ........... B23B 51/0045 408/153 |

(Continued)

FOREIGN PATENT DOCUMENTS

| DE | 102006007232 A1 | 8/2007 |
| DE | 102010046419 A1 | 3/2012 |

(Continued)

OTHER PUBLICATIONS

European Search Report Application No. 15 00 0497 Completed: Jul. 14, 2013; dated Jul. 23, 2015 5 pages.

*Primary Examiner* — David Bates
(74) *Attorney, Agent, or Firm* — Whitmyer IP Group LLC

(57) ABSTRACT

A tool according to the invention for generating an undercut in a bone including a core with a shaft and a stamp mounted on a distal end of the shaft, wherein the stamp, in a transition area to the shaft, has a run-on bevel ascending in the distal direction, and a cutting sleeve which is arranged to be longitudinally movable on the shaft and of which the distal end is formed by at least one segment that can be spread open when pushed onto the run-on bevel, wherein the at least one segment has at least one laterally arranged cutting edge. The invention also relates to a method for generating an undercut in a bone.

17 Claims, 7 Drawing Sheets

(56) References Cited

U.S. PATENT DOCUMENTS

| | | | |
|---|---|---|---|
| 5,928,239 A | 7/1999 | Mirza | |
| 6,293,743 B1* | 9/2001 | Ernst | F16B 13/066 411/24 |
| 6,851,492 B2* | 2/2005 | Sato | B23B 51/0027 175/273 |
| 8,114,084 B2* | 2/2012 | Betts | A61B 17/1617 606/79 |
| 8,221,479 B2* | 7/2012 | Glazer | A61B 17/686 411/58 |
| 9,574,594 B2* | 2/2017 | Imm | F16B 19/1081 |
| 2008/0208230 A1 | 8/2008 | Chin et al. | |
| 2010/0331881 A1 | 12/2010 | Hart | |
| 2013/0138110 A1 | 5/2013 | Hacking | |
| 2014/0276844 A1* | 9/2014 | Bourque | A61B 17/1714 606/80 |
| 2015/0313611 A1* | 11/2015 | O'Farrill | A61B 17/1617 606/80 |

FOREIGN PATENT DOCUMENTS

| | | |
|---|---|---|
| EP | 2098177 A1 | 9/2009 |
| WO | 2007047065 A1 | 4/2007 |
| WO | 2014089198 A1 | 6/2014 |

\* cited by examiner

TOOL AND METHOD FOR GENERATING AN UNDERCUT IN A BONE

FIELD OF THE INVENTION

The present invention relates to a tool and a method for generating an undercut in a human or animal bone, in particular for generating an undercut in a bore that has been introduced into the bone for securing a bone anchor.

BACKGROUND OF THE INVENTION

In order to secure soft tissue, for example a ligament or a tendon, to a bone, it is known to introduce a bore, in particular in the form of a blind hole, into the bone and to insert a bone anchor into the bore. The bone anchor remains in the bone and provides a firm hold for a thread, a band or another connecting means with which the soft tissue is secured on the bone. In this way, for example in the event of an injury, ruptured soft tissue parts can be fixed at the incision site. Known bone anchors of this kind, designed as implants, often use an interference fit or large thread flanks in order to achieve a secure hold in the bone. Particularly in the case of press-fit implants, for example an impaction anchor with ribs, or in the case of interference screws, the external diameter of the implant is greater than the diameter of the bore. To achieve the secure hold, a force is applied from the inside to the wall of the bore, which in extreme cases can lead to a fracture of the bone.

It is also known to generate an undercut in a bore introduced into a bone, particularly in a blind hole, thereby creating a cavity in which a bone anchor can be held with a form fit. U.S. Pat. No. 5,928,239 discloses a surgical device for generating a cavity in a bone, which device has an elongate shaft and a cutting tip, which is arranged with a freely rotatable hinge on the tip of the shaft. By rotation of the shaft at a sufficient speed, the cutting tip is deflected to a pivoted position and thereby generates a cavity, of which the radius is defined by the length of the cutting tip. From EP 2 098 177 A1, a surgical instrument with a shaft is known in which a cutting element is secured on the distal end of the shaft, which cutting element can be brought from a position in alignment with the longitudinal axis of the shaft to a deflected position. According to WO 2007/047065 A1, a surgical instrument for generating a cavity has a lateral window at the distal end of a shaft, wherein a blade, pick or tip can be brought from a position inside the shaft to a position at least partially protruding from the window. However, these known tools have a relatively complex structure and are not optimal in terms of their handling during use, particularly in the case of bores with small diameters.

The international patent application WO 2014/089198 A1, unpublished at the priority date of the invention, discloses a cannulated retrograde reamer with a drill bit, an elongate outer tubular shaft, and one or more cutting elements. By movement of the outer tubular shaft in the direction of the drill bit, the cutting elements come up against an abutment of the drill bit and rotate outward. The reamer can be used with a guide wire.

SUMMARY OF THE INVENTION

The object of the present invention is to make available a tool for generating an undercut in a bone, which tool is of simple construction and/or provides improved handling for simple, quick and low-risk generation of a cavity with an undercut in a bone. It is also the object of the invention to make available an improved method for generating an undercut in a bone.

This object is achieved by a tool according to the invention.

Advantageous developments of the invention are set forth in the dependent claims.

A tool according to the invention for generating an undercut in a bone of a human or animal, in particular in a blind hole introduced into the bone, comprises a core, which comprises an elongate shaft and a stamp mounted on the distal end of the shaft, i.e. the end remote from the user. The shaft has a smaller external diameter than the stamp. The shaft and the stamp can be solid or hollow. The stamp is preferably connected fixedly to the shaft. In a transition area to the shaft, the stamp has a run-on bevel ascending in the distal direction. The run-on bevel can in particular be a run-on surface which widens in the distal direction and which is rotationally symmetrical with respect to a longitudinal axis of the core. The stamp can be substantially cylindrical, wherein, in the proximal end area of the stamp, i.e. the end area closer to the user, the jacket surface of the stamp merges via the run-on bevel or the run-on surface into the jacket surface of the likewise substantially cylindrical shaft. The cylindrical design of the stamp facilitates the insertion of the stamp into the prepared bore in the bone and makes it easier to guide and center the stamp in the bore. The stamp is preferably closed at the distal end and is provided along the distal edge with a chamfer, in order to permit non-traumatic insertion into the bore. In particular, the stamp can be made blunt at the distal end, in which case the distal end of the stamp is preferably formed by a convexly curved surface or a plane surface which lies perpendicular to a longitudinal axis of the shaft and which extends substantially across the entire width of the stamp and can have a chamfered edge.

The tool according to the invention moreover comprises a cutting sleeve which is arranged to be longitudinally movable on the shaft of the core. The cutting sleeve is substantially tubular and at least partially encloses the shaft of the core. The distal end of the cutting sleeve is formed as at least one segment which is connected pivotably to a shaft of the cutting sleeve in such a way that it can be spread laterally open when pushed onto the run-on bevel. Thus, in a first position which it adopts when it is not touching the run-on bevel, the segment is arranged within a continuation of the outer contour of the shaft of the cutting sleeve and, when pushed onto the run-on bevel, is pivoted to a second position in which it protrudes from the outer contour of the cutting sleeve. In particular, the cutting sleeve can be made in one piece with the at least one segment. Preferably, the outer contour of the stamp is flush with the outer contour of the cutting sleeve, such that the tool has substantially a cylindrical shape when the cutting sleeve has been pushed onto the shaft of the core but the segment has not yet spread open. In this state, the tool can be easily inserted into a bore made in a bone, which bore has an internal diameter greater than or corresponding to the external diameter of the stamp and of the cutting sleeve; provision can also be made that the stamp is inserted first into the bore and the cutting sleeve is then inserted after it.

The at least one segment has a laterally arranged cutting edge. By rotation of the cutting sleeve about its longitudinal axis, the cutting edge, which can also be designed as the blade of a cutting knife, can be moved in a tangential direction to which the cutting edge is perpendicular or directed obliquely. The cutting edge can cut into tissue that surrounds the tool circumferentially. In particular, bone material forming the wall of the bore into which the tool has been introduced can be removed in this way. The at least one segment can also be designed to remove tissue by moving in the axial direction and, for this purpose, can likewise have a cutting edge or a cutting knife on its front face, for example. The cutting sleeve can thus also be designed as a drill sleeve. The cutting sleeve and/or the core can be designed for single use or repeated use.

By virtue of the fact that the tool comprises a core with a stamp which has a proximally formed run-on surface, and that a distal segment of the cutting sleeve with a lateral cutting edge can be spread open when pushed onto the run-on surface, it is possible to remove bone tissue in the lateral direction, in a bore formed in a bone, by rotation of the cutting sleeve. By pushing the cutting sleeve onto the run-on surface and rotating it, a cavity with an undercut can be created in a blind hole, into which cavity a bone anchor can be inserted with a form fit. The depth of the undercut or the diameter of the cavity can be controlled by the extent to which the segment is pushed onto the run-on bevel, while the extent of the cavity in the longitudinal direction of the tool can be determined by a common longitudinal movement of core and cutting sleeve. In this way, a simply constructed tool, which can be operated safely and easily, in particular without application of great force, is provided to generate an undercut in a bore that has been introduced into a bone.

According to a preferred embodiment of the invention, the distal end of the cutting sleeve is formed as a plurality of segments which are formed by slits introduced distally into the distal end of the cutting sleeve. At least one of the segments, preferably all of the segments, each have at least one laterally arranged cutting edge. By introducing slits into the distal end of the cutting sleeve, several segments with laterally arranged edges can easily be generated, which can each serve as cutting edges. The cutting edges can be formed by the edge of the slits, which can be a sharp edge, or can be blades of cutting knives arranged at the edge of the slits. The one or more segments can also have cutting edges on both sides, in order to permit, during rotation, a cutting action in both directions of the rotation. By means of the several segments arranged next to each other, bone tissue can be removed particularly effectively by a rotation of the cutting sleeve about its longitudinal axis. Moreover, particularly simple production of the cutting sleeve is made possible by introducing slits into the distal end of a tube.

The slits or the cutting edges formed by the slits and, if appropriate, cutting knives arranged on the cutting edges can have a parallel or oblique orientation with respect to the longitudinal axis. Particularly in the case of an oblique design, for example a helical design, of the cutting edges or slits, it is possible to achieve an improved cutting action, and tissue parts that have been cut out can be more easily transported away.

The at least one cutting edge of the at least one segment is preferably curved and/or toothed, and, if the cutting action is achieved by a cutting knife arranged on an edge of the at least one segment, this applies to the one or more cutting knives. A curved cutting edge can be continuously curved, such that a rounding is obtained in a longitudinal section, or can also have an outwardly oriented corner or tip. It is thereby possible to achieve a still further improved tissue-removing action.

Advantageously, the at least one segment can have a leading edge and a trailing edge in relation to a predefined rotational direction of the cutting sleeve, wherein the leading edge is designed at least partially as a cutting edge; the trailing edge does not have to be designed as a cutting edge. In particular, provision can be made that the trailing edge lies deeper than the leading edge in relation to the longitudinal axis of the cutting sleeve. The trailing edge is therefore arranged at a smaller radius than the leading edge. An outer face of the at least one segment connecting the leading edge to the trailing edge is accordingly inclined with respect to a tangential direction. In this way, it is possible for the leading edge to cut particularly effectively into the laterally arranged tissue, while at the same time the tissue chips that have been cut out are transported away in an improved manner.

Preferably, a transition area between the at least one segment and the shaft of the cutting sleeve is weakened. This can be achieved, for example, by thinning of material, for example by a groove or notch introduced from the inside or outside into the transition area, or by use of another material at the base of the segments such that less force is needed to bend and thus spread open the at least one segment in the transition area when it is pushed onto the run-on bevel. In this way, the spreading open and therefore the operation of the tool are further facilitated, and the durability of a tool designed for repeated use is improved.

The cutting sleeve, at feast the transition area between the segment and the shaft of the cutting sleeve, can advantageously be made of an elastic material. Such a material can be, for example, spring steel, nitinol or another elastic metallic or also non-metallic material. The segment itself and/or the shaft of the cutting sleeve can likewise have the elastic material or be made of it. After the at least one segment has been spread open by bending in the transition area, it is returned to its original position lying within the continuation of the outer contour of the shaft of the cutting sleeve, this return being effected by the restoring force generated by the elastic material when the cutting sleeve is pulled back from the run-on bevel. In this way, it is easier to pull the tool back after the undercut has been introduced into the bone, and the bone material forming the undercut is protected.

According to a preferred embodiment of the invention, a distal inner edge of the cutting sleeve or of the at least one segment is rounded or has a chamfer. This reduces the friction during the pushing movement onto the run-on bevel and makes the tool easier to operate. In addition, a lateral inner edge of the at least one segment can also be rounded or have a chamfer; this is advantageous particularly in the case where the core is not rotated during the rotation of the cutting sleeve for removal of tissue.

Preferably, the run-on bevel is approximately conical, in particular bell-shaped. A conically shaped run-on surface permits particularly effective and simultaneous spreading open of all the segments forming the distal end of the cutting sleeve, when the cutting sleeve is pushed onto the run-on bevel. The run-on bevel can in particular have a curved profile in longitudinal section, preferably one that ascends in the distal direction with increasing pitch. In this way, the at least one segment can be spread open by a uniform force or by a force that increases with increasing spreading open, and the handling of the tool is thus made easier. In particular, a bell-shaped run-on surface permits particularly easily controlled spreading open of a plurality of segments at the distal end of the cutting sleeve.

According to a preferred embodiment of the invention, the shaft of the core, or a transition area between the stamp and the shaft of the core, has an abutment which acts in the axial direction and which cooperates with a corresponding abutment of the cutting sleeve in order to limit an axial travel of the cutting sleeve relative to the core. In particular, the abutment of the core and the abutment of the cutting sleeve can each be designed as steps that allow the cutting sleeve to move relative to the core up to a predefined maximum travel, at which a spreading open of the at least one segment corresponds to a predefined diameter of the cavity that is to be generated. This makes it easier to generate an undercut that is exactly right for a defined use or a defined implant.

It is also preferable that an axially continuous gap is arranged between the shaft of the core and the cutting sleeve, through which gap a flushing liquid can be conveyed. This permits flushing, such that bone chips or other tissue parts that have been cut out can be transported away, and cooling, such that overheating of the tool or of the surrounding bone tissue can be avoided during operation. To allow the cutting sleeve to be safely guided on the shaft of the core, it is possible for guide means, for example guide ribs, to be arranged on the outer face of the shaft of the core and/or on the inner face of the shaft of the cutting sleeve, which guide means extend in the longitudinal direction, and between which the axially continuous gap remains for the passage of flushing liquid.

Advantageously, the shaft of the core can be designed with an axially continuous hollow space and the stamp can be at least partially hollow, wherein a hollow space formed within the stamp is connected to the continuous hollow space of the shaft of the core, and wherein the stamp has lateral apertures. The apertures can be arranged in a cylindrical portion of the stamp and/or in the area of the run-on bevel or in the run-on surface. This permits the flow of flushing liquid for transporting bone chips or other tissue parts away and for cooling.

According to a particularly preferred embodiment, provision is made for both an axially continuous gap between the shaft of the core and the cutting sleeve and also a hollow space arranged inside the core and continuing into the stamp, wherein the hollow space of the core communicates, via apertures in the stamp, with the area outside the stamp. This permits a continuous through-flow of flushing liquid, allows removed tissue parts to be transported away in a particularly effective manner, and ensures particularly effective cooling. Thus, for example, flushing liquid can be delivered through the gap between the shaft of the core and the cutting sleeve, and flushing liquid can be suctioned through the apertures in the stamp, the hollow space inside the stamp and the hollow space inside the shaft of the core. This further improves the usability of the tool according to the invention. One or more ports for connection to a flushing and suctioning mechanism can be arranged at a distal end of the tool.

The invention also relates to a core with a shaft and with a stamp mounted on a distal end of the shaft, wherein the core is designed for use in a tool according to the invention and in particular as has been described above.

The invention moreover relates to a cutting sleeve for use in a tool according to the invention. The cutting sleeve has in particular the above-described features of the cutting sleeve and is designed in such a way that it can be arranged in a longitudinally movable manner on a core that is designed as has been described above.

The invention further relates to a combination of a cutting sleeve and of a core, wherein the cutting sleeve can be pushed onto the core and, in this way, it is possible to create a tool that is designed as has been described above.

In a method according to the invention for generating an undercut in a human or animal bone, a tool is used that is designed as has been described above. The method starts out from a drilled channel, in particular a blind hole, which has been prepared beforehand in the bone in a manner known per se.

To carry out the method according to the invention, a cutting sleeve is pushed onto the shaft of a core, wherein the cutting sleeve and the core are designed as has been described above. The cutting sleeve is advanced onto the shaft of the core to an extent such that the at least one segment is not yet spread open over the run-on bevel. The core, and the cutting sleeve placed thereon, are inserted into the drilled hole and are together advanced in the drilled hole until the distal end area of the cutting sleeve is arranged in an area of the drilled hole in which a cavity with an undercut is to be prepared; in particular, the stamp of the core can be advanced as far as the bottom of the blind hole. Alternatively, the core can be inserted first into the drilled hole and, thereafter, the cutting sleeve can be guided over the shaft of the core. It is also possible that a drill, with which the bore has been generated, is designed as a core and remains in the drilled hole after the bore has been formed, and the cutting sleeve is advanced over the shaft of the core in order to generate the undercut.

The cutting sleeve is now at the latest moved in rotation and advanced farther in the distal direction such that, when it meets the run-on bevel, the at least one segment is spread open and rotates about the longitudinal axis of the cutting sleeve. By means of the rotation movement, the cutting edge of the at least one segment removes bone tissue from the wall of the blind hole, wherein the diameter of a cavity thus generated is defined by the extent to which the cutting sleeve is pushed onto the run-on bevel of the core. The length of the cavity generated with the aid of the undercut is defined by joint axial movement of the core and of the cutting sleeve pushed onto the run-on bevel. In particular, the core and the cutting sleeve can be pulled back together during rotation in order to generate an undercut starting from the bottom of the blind hole or, depending on the length of the stamp, near the bottom of the blind hole.

After a cavity with the desired dimensions has been generated, the cutting sleeve is pulled back, if appropriate after a slight advance of the core, such that the at least one segment springs back, or is forced back by contact with the bone material, and again comes to lie within the continuation of the outer contour of the cutting sleeve. The cutting sleeve and the core are thereafter removed from the drilled hole.

To achieve a rotation movement, the cutting sleeve can be connected to a mechanical or electrical drive, which can be designed for example in the manner of the drive of a surgical drill or morcellator. Moreover, a connection to an external flushing and suctioning mechanism can be produced, in order to permit flushing through a hollow space arranged between the shaft of the core and the cutting sleeve and also through apertures in the wall of the stamp and through an adjoining hollow space in the latter and in the shaft of the core. In this way, tissue fragments arising during the formation of the undercut can be removed; at the same time, excessive heating of the tool and of the space inside the bone can be avoided. The connection to the drive and to the flushing and suctioning mechanism is preferably produced before the cutting sleeve is pushed into the drilled hole, although it can also be established afterward.

In the hollow space thus generated inside the bone, it is then possible for an implant, for example a bone anchor, to be inserted through the drilled hole and to be anchored with a form fit by expanding in the cavity and preferably filling it. A bone anchor suitable for this purpose is known from US 2010/0331881 A1, for example.

The core is preferably stationary during the formation of the undercut, i.e. the shaft of the core is not driven by a drill drive. The cutting sleeve thus rotates on the core, and the at least one segment rotates on the in particular conical or bell-shaped run-on surface of the stamp. In this case, the inner face of the at least one segment is particularly preferably rounded; in particular, the lateral inner edges of the at least one segment are rounded or have a chamfer in order to reduce the friction on the run-on surface of the stamp. Since the stamp inserted into the blind hole is stationary in this variant of the method, particularly reliable guiding of the cutting sleeve is ensured; moreover, overheating of bone tissue in the area of the bottom of the blind hole can be particularly reliably avoided.

Alternatively, the core can rotate together with the cutting sleeve during the formation of the undercut. In this case, it is possible to avoid the development of frictional wear between the at least one spread-open segment and the run-on bevel of the stamp; moreover, the drive can be of a particularly simple configuration. In this case, the run-on bevel can be adapted to the number and arrangement of the spreadable segments and, for example, can be designed only on one side if just a single segment is provided. Overheating of the bone tissue remaining at the edge of the cavity can likewise be avoided by flushing.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

Further aspects of the invention will become clear from the following description of a preferred illustrative embodiment and from the attached drawing, in which.

DETAILED DESCRIPTION OF THE INVENTION

Figure 1A:
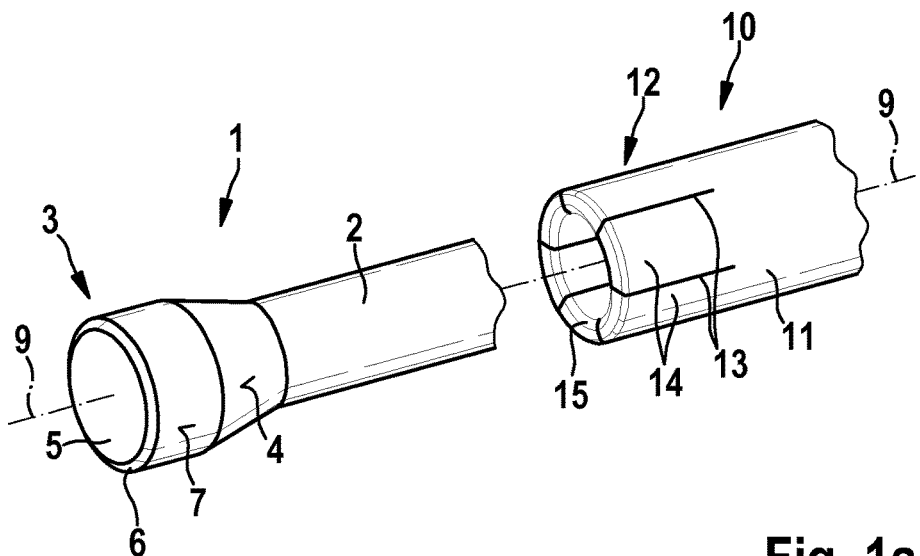
FIGS. 1a to 1c show a first illustrative embodiment of a tool according to the invention in three different axial relative positions of cutting sleeve and core.

According to a first embodiment, shown in FIG. 1a, a tool according to the invention is composed of a core 1 and of a cutting sleeve 10, wherein the core 1 is composed of a cylindrical shaft 2 and of a stamp 3 mounted at the distal end of the latter. The stamp 3 is likewise designed substantially cylindrically and has a greater external diameter than the shaft 2. In its proximal end area, the stamp has a substantially conical run-on surface 4, of which the diameter widens distally from the diameter of the shaft 2 to the external diameter of the stamp 3. At the distal end, the stamp 3 is closed by a front wall 5 which, at the edge, merges with a chamfer 6 into the jacket surface 7 of the stamp 3.

As is shown in FIG. 1a, the cutting sleeve 10 comprises a cylindrical shaft 11, of which the distal end area 12 is divided into a plurality of segments 14 by a plurality of slits 13 extending in the longitudinal direction. The segments have a chamfer or a rounding 15 on their distal inner face. The internal diameter of the shaft 11 of the cutting sleeve 10 is matched to the external diameter of the shaft 2 of the core 1 in such a way that the cutting sleeve is longitudinally movable on the shaft 2 of the core 1, in particular being able to be pushed over the shaft 2 from the proximal direction. The external diameter of the cutting sleeve 10 matches that of the stamp 3. For explanatory purposes, the wall thickness of the cutting sleeve 10 in FIG. 1a and in the further figures is shown larger in relation to the diameter than is preferred in the described illustrative embodiments. A handle or a coupling for connection to a drive can be provided (not shown) at the proximal end of the cutting sleeve 10 or of the core 2.

Figure 1B:
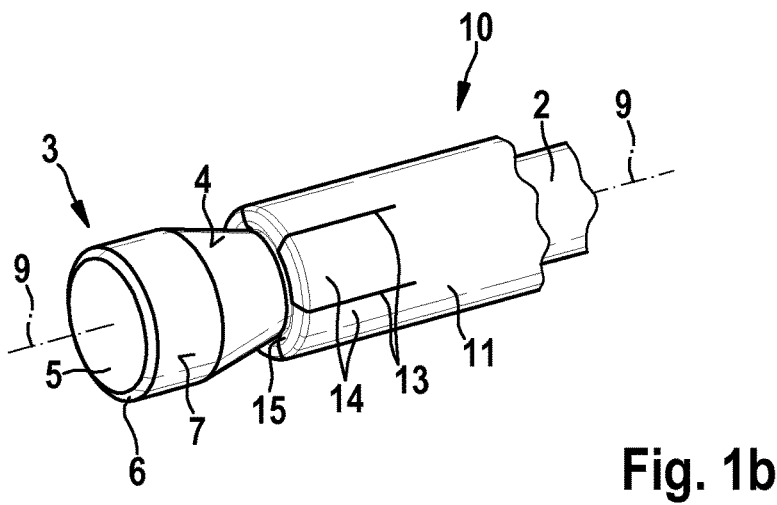
Figure 1C:
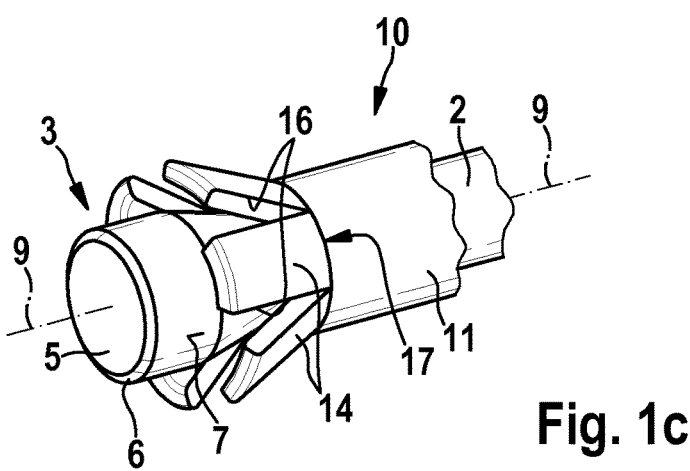

FIG. 1b shows the cutting sleeve 10 in a position in which it has been pushed distally over the shaft 2 of the core to such an extent that the segments 14 touch or almost touch the run-on surface 4 but are not yet spread open. As is indicated in FIGS. 1a to 1c, the cutting sleeve 10 and the core 1, when pushed one onto the other, are arranged coaxially with respect to a common longitudinal axis 9. If the cutting sleeve 10 is now advanced farther in the distal direction, the segments 14 are spread open by being pushed onto the run-on surface 4 and, in this way, they protrude beyond the outer contour of the arrangement of core 1 and cutting sleeve 10 (FIG. 1c). A transition area 17 between the segments 14 and the shaft 11 of the cutting sleeve acts as a hinge and, for this purpose, is designed to be elastically bendable. The pushing on and spreading open are made easier by the rounding 15 on the distal inner edge of the segments 14. Each segment 14 has a cutting edge 16 on a lateral outer edge. By the spreading open of the segments 14 and the rotation of the cutting sleeve 10 about its longitudinal axis 9, the cutting edges 16 can cut into surrounding tissue and remove the latter.

Figure 2:
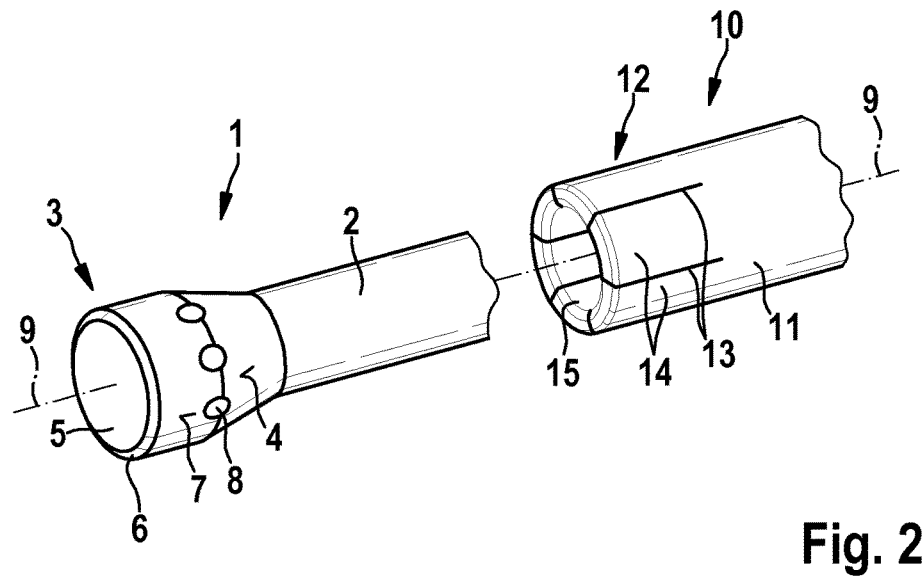
FIG. 2 shows a second illustrative embodiment of a tool according to the invention.

According to the second embodiment of the invention, shown in FIG. 2, the shaft 2 and the stamp 3 can each have an inner hollow space, wherein the hollow space of the shaft 2 is connected to that of the stamp 3 and is designed extending as far as the proximal end of the shaft 2 for connection to suction (not shown). The jacket surface 7 of the stamp 3 has a number of apertures 8 which extend into the run-on surface 4 and through which the hollow space of the stamp 3 communicates with the outside. The internal diameter of the cutting sleeve of the shaft 11 of the cutting sleeve 10 is greater than the external diameter of the shaft 2 of the core 1, such that flushing liquid can be guided into the area of the run-on surface 4 by way of the gap thus formed. A flushing port (not shown) can be provided for this purpose on the proximal end of the cutting sleeve 10. In this way, a closed flushing circuit can be created for carrying away bone tissue that has been removed by the cutting edges 16. Flushing and suction ports, and a handle or a coupling for connection to a drive, are arranged in the proximal end area (not shown) of the shaft 2 of the core 1 and of the cutting sleeve 10.

Figure 3A:
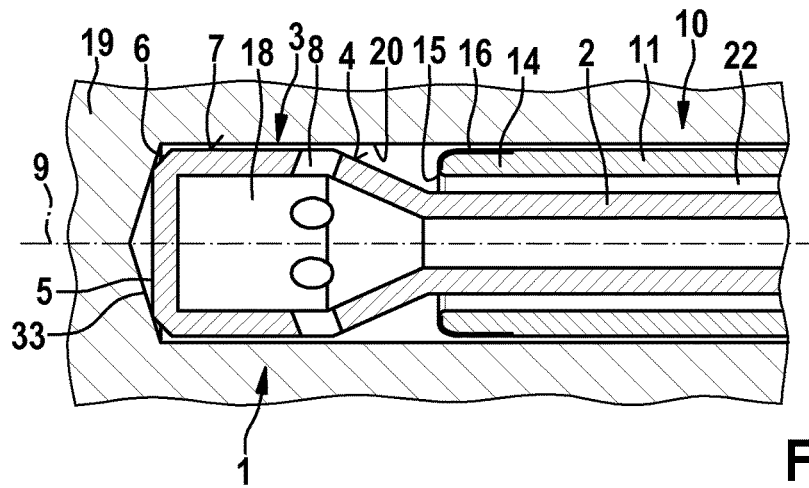
FIGS. 3a and 3b show the tool according to FIG. 2 in sectional views in two different axial relative positions.
Figure 3B:
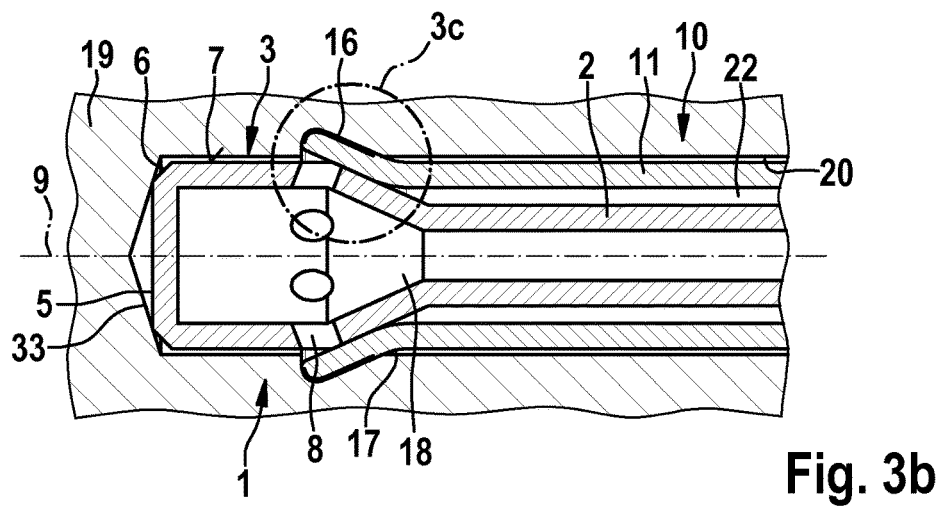
Figure 3C:
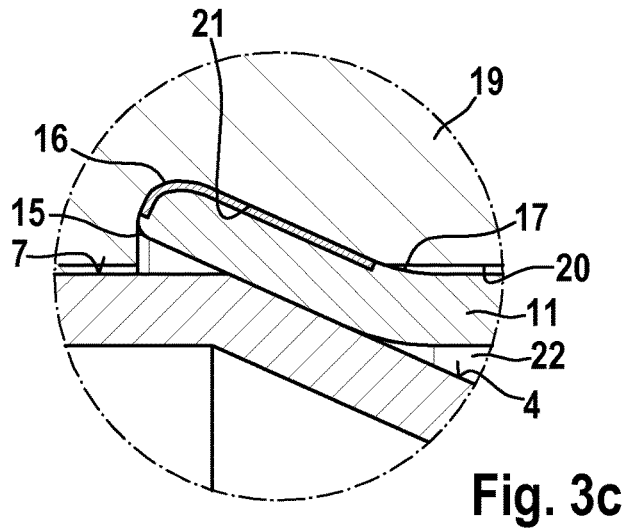
FIG. 3c shows an enlarged detail from FIG. 3b.

In FIGS. 3a and 3b, the tool according to FIG. 2 is shown in two relative positions corresponding to the situations shown for the first embodiment in FIGS. 1b and 1c, in each case in a sectional view cut in the longitudinal direction; FIG. 3c shows an enlarged detail. In the position of the cutting sleeve 10 shown in FIG. 3a, the segments 14 lie within the outer contour defined by the outer face of the shaft 11 of the cutting sleeve 10 and by the jacket surface 7 of the stamp 3. When pushed onto the run-on surface 4, the segments 14 are spread open and then protrude beyond the outer contour (FIG. 3b). As is shown in an enlarged view in FIG. 3c, the distal inner edge of the segments 14 is provided with a rounding 15 in order to reduce friction and wear when sliding on the run-on surface 4. Moreover, on at least one side of each segment 14, an edge obtained from the formation of the slit 13 is configured as cutting edge 16. The cutting edge 16 is rounded in a longitudinal profile and extends in the proximal direction into the transition area 17 between the segment 14 in question and the shaft 11 of the cutting sleeve 10 or close thereto, in order to make production of the undercut 21 easier. In order to be able to remove tissue also during a movement in the distal direction, the cutting edge 16 extends as far as or into the rounding 15.

As is shown in FIGS. 3a to 3c, the core 1, a distal portion of the shaft 2 of the core 1, the segments 14 and a distal portion of the shaft 11 of the cutting sleeve 10 are inserted into a bore 20 which has been introduced into a bone 19 and which is designed as a blind hole with a conical bottom 33. The external diameter of the stamp 3 and of the cutting sleeve 10 is slightly smaller than the internal diameter of the bore 20, in order to facilitate the insertion into the bore 20. Moreover, flushing is made easier in this way. For flushing, flushing liquid is delivered through a continuous gap 22 running between the shaft 2 of the core 1 and the shaft 11 of the cutting sleeve 10, passes through the work area of the cutting edges 16, flows through the apertures 8 into the hollow space 18 arranged inside the stamp 3 and the shaft 2 of the core, and is carried off through these in the proximal direction. Flushing and suction ports, and a coupling for connection to a drive, are arranged in the proximal end area (not shown) of the shaft 2 of the core 1 and of the cutting sleeve 10.

To generate an undercut 21 in the bore 20, the core 1 and the cutting sleeve 10 are inserted together or in succession into the bore 20 until the stamp 3 bears with its front wall 5 on the bottom of the blind hole (FIG. 3a). The cutting sleeve 10 is then rotated about the longitudinal axis 9 and moved farther in the distal direction relative to the core 1, in order to spread the segments 14 open and introduce an undercut 21 into the side wall of the bore 20 (FIGS. 3b and 3c).

Figure 4A:
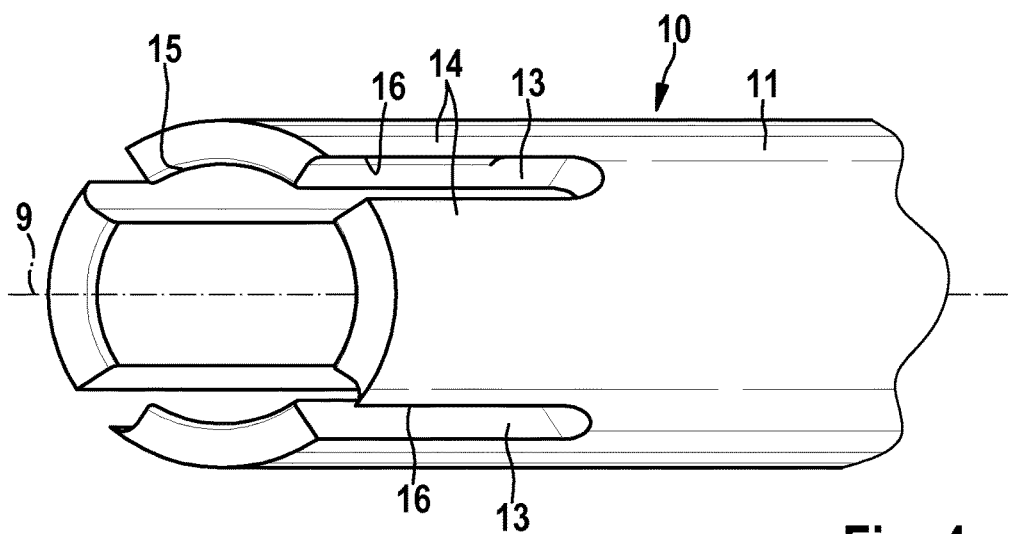
FIGS. 4a and 4b show a third illustrative embodiment of a tool according to the invention with the cutting sleeve in an oblique view (FIG. 4a) and the tool with the cutting sleeve in a sectional view (FIG. 4b)
Figure 4B:
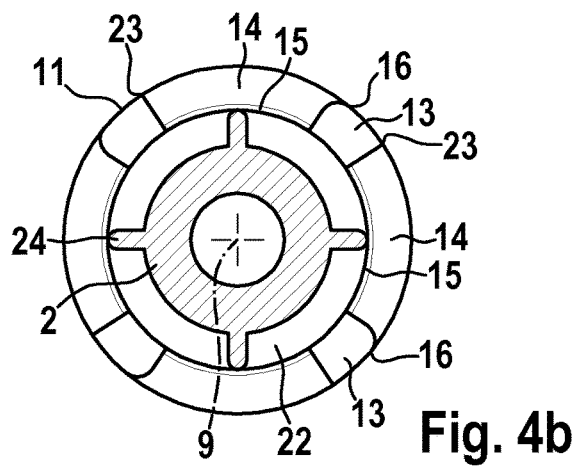

In FIGS. 4a and 4b, a third illustrative embodiment of the invention is shown in two different views, wherein in FIG. 4b the cutting sleeve 10 pushed onto the shaft 2 of the core 1 is sectioned transverse to the longitudinal axis in the area of the segments 14. The slits 13 introduced distally into the cutting sleeve 10 are made wide in order to create sufficient space for flushing liquid to flow through. Moreover, as can be seen from FIGS. 4a and 4b, the cutting edge 16 is designed as a tangentially projecting blade on a side wall of the slit 13. A particularly effective removal of bone material is permitted in this way. A direction of rotation during the operation of the tool is predefined, with the cutting edge 16 being arranged on the leading edge of the segment 14. The trailing edge 23 has no blade. Moreover, on its outer face, the shaft 2 of the core 1 carries a plurality of ribs 24, which extend in the longitudinal direction and divide the gap 22 into hollow spaces which extend in the longitudinal direction and through which flushing liquid can be guided into the area of the cutting edges 16 and which additionally ensure reliable guidance of the shaft 11 of the cutting sleeve 10 on the shaft 2 of the core 1. Otherwise, the cutting sleeve 10 and the core 1 are designed as described above.

Figure 5:
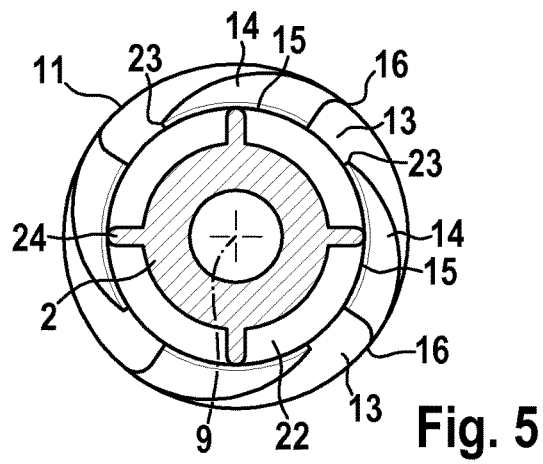
FIG. 5 shows a fourth illustrative embodiment of a tool according to the invention in a sectional view.

In a fourth illustrative embodiment of the invention as shown in FIG. 5, in a view corresponding to FIG. 4b, the outer faces of the segments 14 can run obliquely, such that the leading edge, which is designed as the cutting edge 16, is higher than the trailing edge 23. In this way, the cutting action and the removal of the generated bone chips is further improved. Otherwise, the fourth illustrative embodiment corresponds to the third illustrative embodiment shown in FIGS. 4a and 4b.

Figure 6:
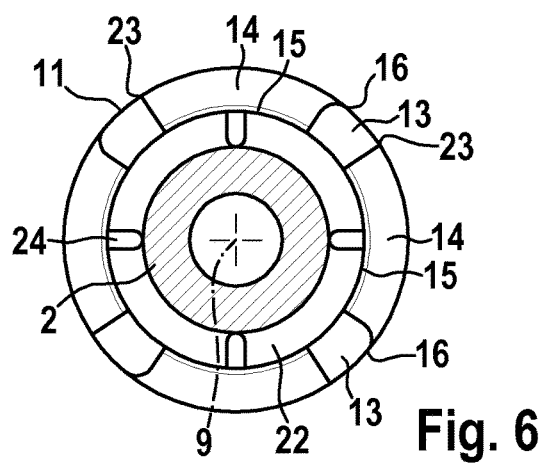
FIG. 6 shows a fifth illustrative embodiment of a tool according to the invention in a sectional view.

FIG. 6, in a view corresponding to FIG. 4b, shows that the ribs 24 can be arranged on the inner face of the shaft 11 of the cutting sleeve 10. In the same way as has been explained with reference to FIG. 4b, the gap 22 is thus divided into axially extending hollow spaces for flushing liquid to pass through; moreover, the ribs 24 serve to reliably guide the cutting sleeve 10 on the shaft 2.

Figure 7:
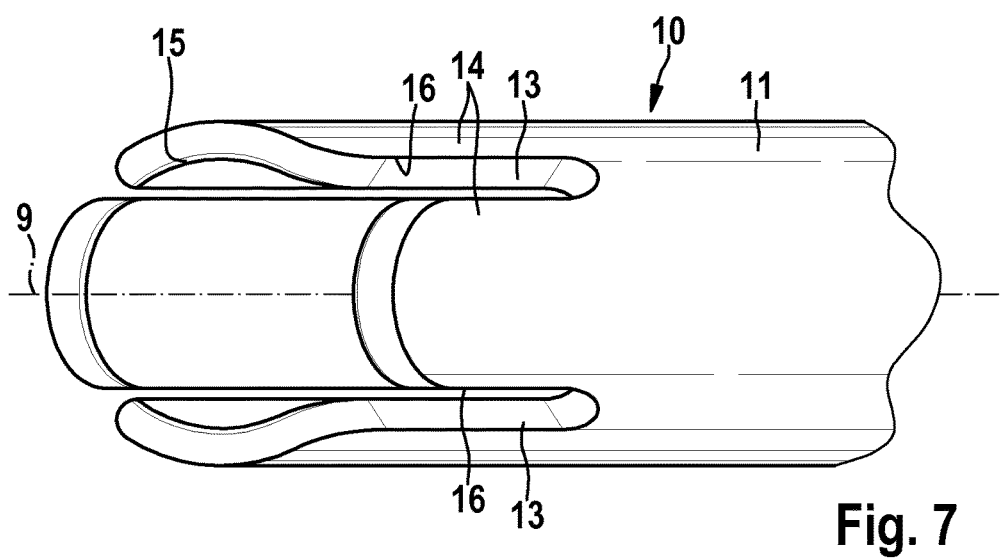
FIG. 7 shows the cutting sleeve according to a sixth illustrative embodiment of a tool according to the invention in an oblique view.

As is shown in FIG. 7, in a further embodiment of the invention, the segments 14 can be rounded at the distal face. The cutting edges 16, which here extend along the outer face of the segments 14, are therefore also curved and reach at least as far as the vertex of the respective segment 14. A cutting sleeve 10 designed in this way permits particularly sensitive removal of bone tissue.

Figure 8A:
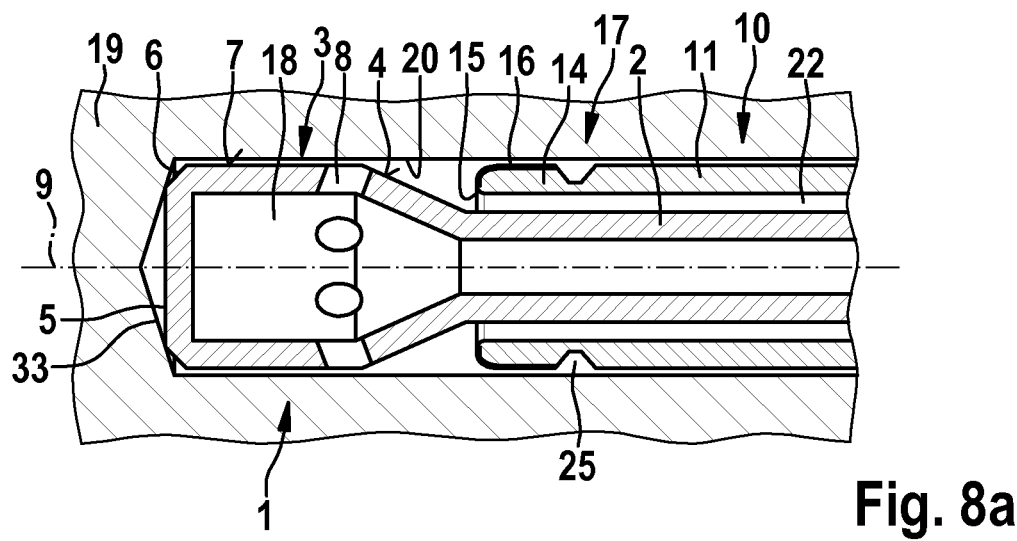
FIGS. 8a and 8b show a seventh illustrative embodiment of a tool according to the invention in sectional views in two different axial relative positions.
Figure 8B:
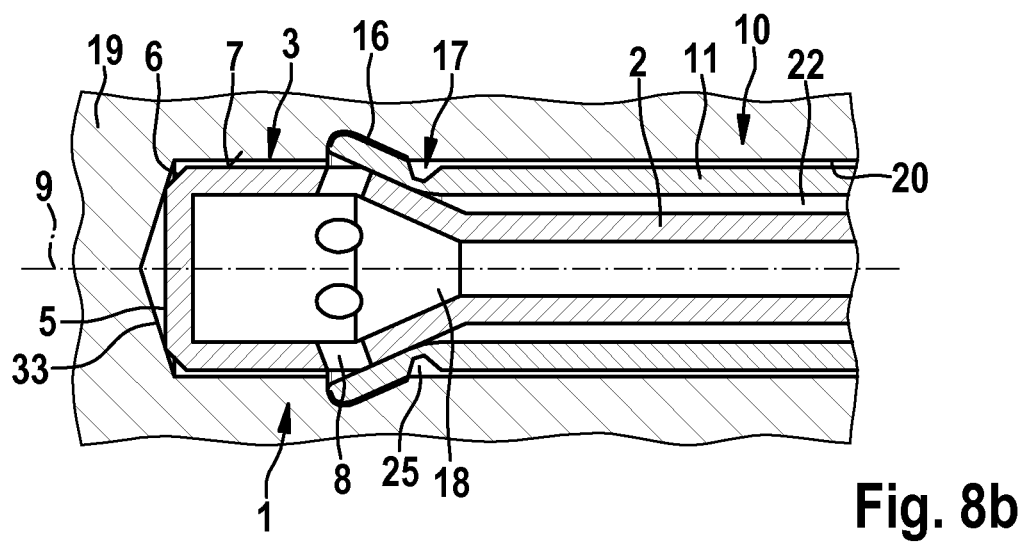

A cutting sleeve 10 according to the illustrative embodiments described above can also be designed in such a way that, in the transition area 17 between the segments 14 and the shaft 11 of the cutting sleeve 10, the wall thickness of the cutting sleeve 10 is reduced in order to permit easier pivoting of the segment 14. For this purpose, for example, a groove or a notch 25 can be formed in the transition area 17, as is shown by way of example in FIGS. 8a and 8b in two different axial relative positions of core 1 and cutting sleeve 10, which correspond to those shown in FIGS. 3a and 3b. Otherwise, the embodiments of the invention shown in FIGS. 6 to 8b correspond to those explained above.

Figure 9:
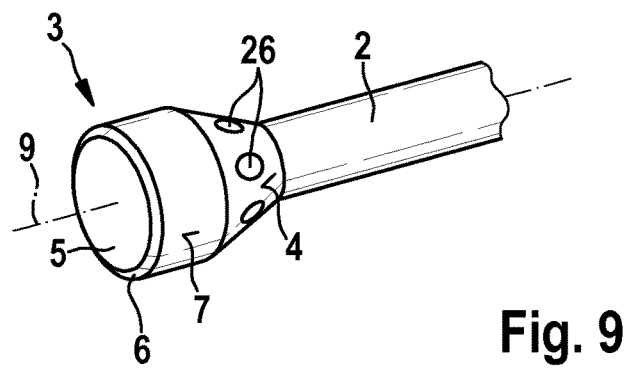
FIG. 9 shows the core according to an eighth illustrative embodiment of the invention.

FIG. 9 shows the stamp 3 of a core 1 according to an eighth embodiment of the invention. Here, the stamp 3 is likewise arranged at the distal end of a shaft 2 and merges with a conical run-on surface 4 into the jacket surface of the shaft 2. The cylindrical area of the stamp 3 has no apertures, but the run-on surface 4 has apertures 26, which can be of elongate shape and form a connection from the outside into the inner hollow space of the stamp 3, which is connected to the continuous hollow space of the shaft 2. To reduce friction caused by the rotation of the segments bearing on the run-on surface 4, the apertures 26 can have rounded edges.

Figure 10:
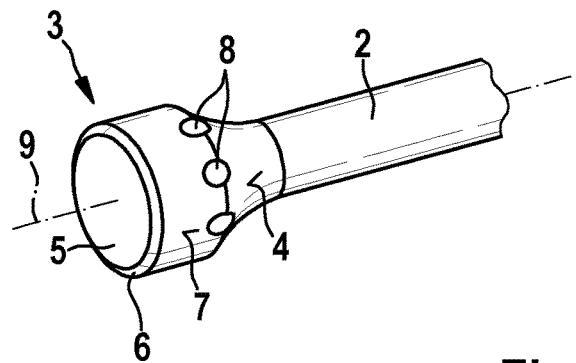
FIG. 10 shows the core according to a ninth illustrative embodiment of the invention.

A further embodiment of a stamp 3 is shown in FIG. 10. Here, the run-on surface 4 is bell-shaped, wherein the pitch of the run-on bevel thus formed increases from proximal to distal. Otherwise, the stamp 3 in the illustrative embodiments shown in FIGS. 9 and 10 is designed as described above and can be used in combination with the cutting sleeves 10 described above. In the illustrative embodiments shown in FIGS. 2a to 3c and in FIG. 10, the run-on surface 4 can also have one or more apertures 26 for improving the flushing action, particularly at the start of the preparation of the undercut.

Figure 11:
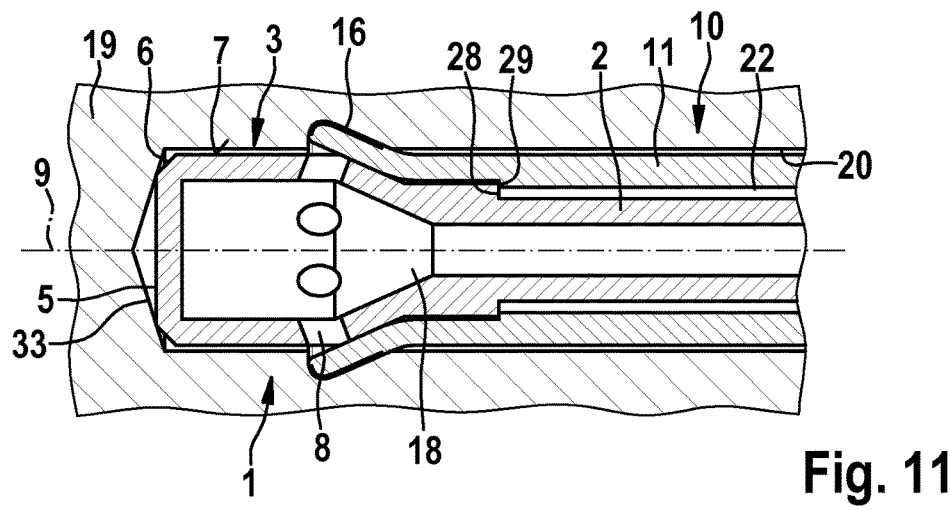
FIG. 11 shows a further illustrative embodiment of a tool according to the invention in a sectional view.

As is shown in FIG. 11, a step 28 can be provided in a distal end area of the shaft 2, which step 28 cooperates with a step 29 on the inner face of the shaft 11 of the cutting sleeve 10 in order to limit the travel in the axial direction. In this way, an external diameter of a cavity to be generated can be established particularly precisely. Otherwise, the illustrative embodiment shown in FIG. 11 is designed like the illustrative embodiments described above.

The description of the illustrative embodiments reveals various possible combinations of a stamp 3 and of a shaft 2, and of a core 1 formed by the stamp 3 and the shaft 2, with a cutting sleeve 10, which combinations are likewise covered by the invention. The stamp 3 according to the illustrative embodiments described above can in particular have an external diameter of approximately 2 to 5 mm. The external diameter of the cutting sleeve 10 is likewise ca. 2 to 5 mm, wherein the cutting sleeve 10 and the segments 14 can have a wall thickness of ca. 0.2 mm, for example. The cutting sleeve 10 is made of an elastic material suitable for surgical use, preferably an elastic metallic material, for example spring steel or nitinol. Such materials allow the segments 14 to bend repeatedly and spring back and also permit the formation of cutting edges 16 that can also remove hard bone material. The stamp 3 and the shaft 2 of the core 1 are made of a metallic or non-metallic material suitable for surgical use, for example stainless steel or polyether ether ketone (PEEK). The core 1 can be made in one piece.

Figure 12:
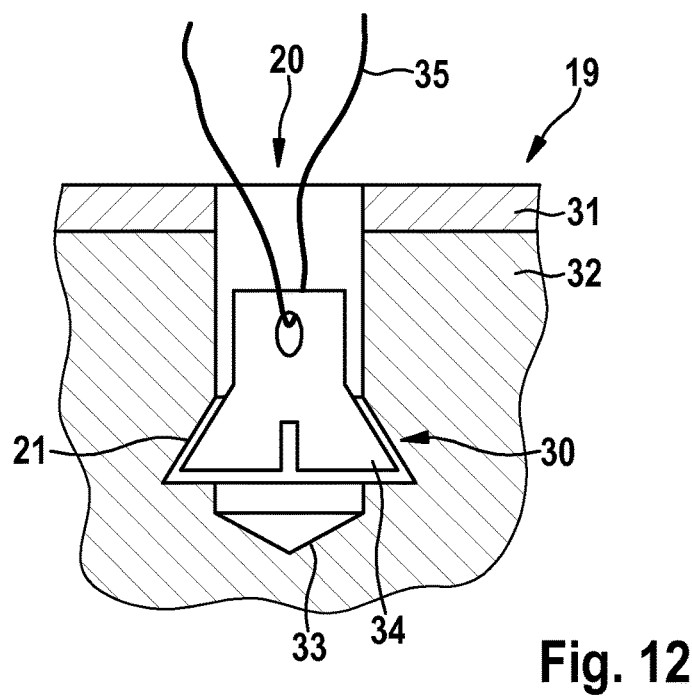
FIG. 12 shows a section through a bone with a cavity created by a method according to the invention, with a bone anchor inserted into said cavity.

FIG. 12 shows a schematic view of an example of a cavity 30 that can be created using a tool according to the invention and a method according to the invention. First of all, a customary surgical bone drill is used to introduce a cylindrical bore 20 into the bone 19. The bore 20 passes through the outer layer (cortical substance 31) and ends in the spongy substance 32 of the bone 19. According to the shape of the drill used, the bottom 33 of the bore 20 generally has a conical shape. After the bore 20 has been formed, the drill is withdrawn again from it.

The stamp 3 of the core 1 is then inserted into the bore 20 until it bears on the bottom 33 of the bore. The cutting sleeve 10 pushed onto the shaft 2 of the core 1 is then inserted into the bore 20 (see FIGS. 1b, 3a and 8a). After coming into contact with the run-on surface 4, the cutting sleeve 10 is pushed farther in the distal direction while rotating about its longitudinal axis, as a result of which the segments 14 are spread open and cut into the surrounding bone tissue (spongy substance 32) (see FIGS. 1c, 3b, 3c and 8b). An undercut 21 is thus formed. Alternatively, the core 1 and the cutting sleeve 10, in the relative position shown in FIGS. 1b, 3a and 8a, can be pushed together into the bore 20 and, after the stamp 3 comes to bear on the bottom 33 of the bore 20, the cutting sleeve can be moved farther in the distal direction. The core 1 is preferably not moved in rotation, although this may also be possible.

When an undercut 21 of sufficient depth has been generated, the cutting sleeve 10 is first of all pulled back in the proximal direction. After sliding off the run-on surface 4, the segments 14 again lie within the continuation of the outer contour of the shaft 11 of the cutting sleeve 10 (see FIGS. 1b, 3a and 8a), such that the cutting sleeve 10 can be removed from the bore 20 without further removal of bone tissue. Thereafter, the core 1 is also removed from the bore 20. A bone anchor 34 then inserted into the cavity 30 formed by the undercut 21 is spread open using an expansion mechanism and is thereby anchored in the cavity 30. The bone anchor 34 thus makes it possible, for example by way of a thread 35, to hold soft tissue or also a surgical implant on the outside of the bone 19.

Figure 13:
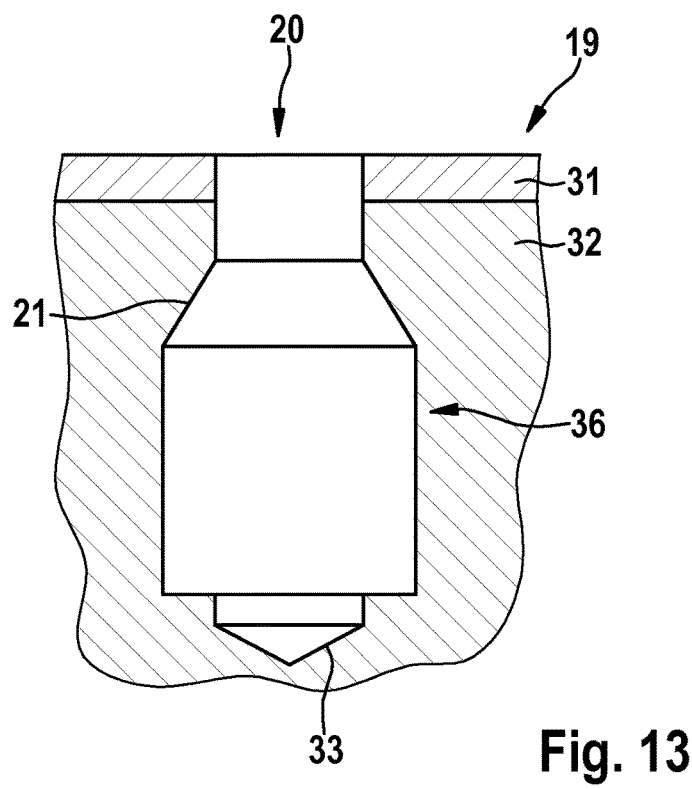
FIG. 13 shows a section through a bone with a cavity created according to a variant of the method according to the invention.

With a tool according to the invention and a method according to the invention, it is also possible for a substantially cylindrical cavity 36 shaped as in FIG. 13 to be created in the bone 19. In this case, the procedure is initially as described with reference to FIG. 12, and, after the segments 14 have been spread open, the core 1 and the cutting sleeve 10 are together moved in the proximal direction, with further rotation of the cutting sleeve 10. When a cavity 36 of sufficient length has formed, the core 1 is held secure or moved slightly in the distal direction, and the cutting sleeve 10 is withdrawn farther from the bore 20 in the proximal direction. The core 1 is then likewise removed from the bore 20.

By the method described with reference to FIGS. 12 and 13, a cavity 30, 36 for fixing a bone anchor with a form fit can be created with dimensions suitable for many applications. Generally, an undercut with a depth of ca. 0.5 mm suffices, i.e. the cavity 30, 36 is widened by ca. 1 mm in diameter compared to the bore. The bone anchor can have a length of ca. 10 mm, for example.

For the sake of clarity, not all reference signs are shown in all of the figures. Reference signs that are not explained in connection with one figure have the same meaning as in the other figures.

LIST OF REFERENCE SIGNS 1 core
2 shaft
3 stamp
4 run-on surface
5 front wall
6 chamfer
7 jacket surface
8 aperture
9 longitudinal axis
10 cutting sleeve
11 shaft
12 distal end area
13 slit
14 segment
15 rounding
16 cutting edge
17 transition area
18 hollow space
19 bone
20 bore
21 undercut
22 gap
23 trading edge
24 rib
25 notch
26 aperture
28 step
29 step
30 cavity
31 cortical substance
32 spongy substance
33 bottom 34 bone anchor
35 thread
36 cavity

The invention claimed is:

1. A tool for generating an undercut in a bone, the tool comprising:
a core with a shaft;
a stamp mounted on a distal end of the shaft, wherein the stamp, in a transition area to the shaft, has a run-on bevel ascending in a distal direction; and
a cutting sleeve which is arranged to be longitudinally movable on the shaft and of which the distal end is formed by at least one segment that can be spread open when pushed onto the run-on bevel, wherein the at least one segment has at least one laterally arranged cutting edge, and wherein the at least one segment has a leading edge and a trailing edge in relation to a predefined rotational direction of the cutting sleeve, wherein the leading edge at least partially defines the at least one laterally arranged cutting edge;
wherein the trailing edge is arranged radially deeper than the leading edge.

2. The tool according to claim 1, wherein the distal end of the cutting sleeve is formed by a plurality of segments which each have at least one laterally arranged cutting edge and which are separated from each other by slits extending into the distal end of the cutting sleeve in a direction toward a proximal end of the cutting sleeve.

3. The tool according to claim 1, wherein the one or more cutting edges are arranged obliquely with respect to a longitudinal axis of the cutting sleeve.

4. The tool according to claim 1, wherein the one or more cutting edges are curved and/or toothed.

5. The tool according to claim 1, wherein a transition area between the at least one segment and a shaft of the cutting sleeve is weakened.

6. The tool according to claim 1, wherein the cutting sleeve is made of an elastic material, at least in a transition area between the at least one segment and a shaft of the cutting sleeve.

7. The tool according to claim 1, wherein a distal inner edge of the at least one segment has a rounding or a chamfer.

8. The tool according to claim 1, wherein the run-on bevel defines a substantially conical or bell-shaped run-on surface.

9. The tool according to claim 1, wherein the shaft of the core or a transition area between the stamp and the shaft of the core has, in an axial direction, an abutment which cooperates with an abutment of the cutting sleeve in order to limit an axial travel of the cutting sleeve relative to the core.

10. The tool according to claim 1, wherein an axially continuous gap is arranged between the shaft of the core and the cutting sleeve.

11. A tool for generating an undercut in a bone, the tool comprising:
a core with a shaft;
a stamp mounted on a distal end of the shaft, wherein the stamp, in a transition area to the shaft, has a run-on bevel ascending in a distal direction; and
a cutting sleeve which is arranged to be longitudinally movable on the shaft and of which the distal end is formed by at least one segment that can be spread open when pushed onto the run-on bevel, wherein the at least one segment has at least one laterally arranged cutting edge;
wherein the stamp and the shaft of the core have an inner hollow space continuing into a proximal end area of the shaft, and the stamp has at least one lateral aperture.

12. A method for generating an undercut in a bone, comprising:
providing a core with an elongate shaft and with a stamp which is mounted on a distal end of the shaft and which, in a transition area to the shaft, has a run-on bevel ascending in a distal direction, and a cutting sleeve, which is longitudinally movable on the shaft and of which a distal end is formed by at least one segment that can be spread open when pushed onto the run-on bevel and has at least one laterally arranged cutting edge, wherein the at least one segment has a leading edge and a trailing edge in relation to a predefined rotational direction of the cutting sleeve, wherein the leading edge at least partially defines the at least one laterally arranged cutting edge, wherein the trailing edge is arranged radially deeper than the leading edge;
inserting a distal portion of the core and a distal portion of the cutting sleeve into a bore that has been introduced into the bone; and
rotating the cutting sleeve and moving the cutting sleeve in the distal direction relative to the core in such a way that the at least one segment is spread open over the run-on bevel and the cutting edge of the at least one segment removes bone tissue from a wall of the bore.

13. The method according to claim 12, wherein the core is not moved in rotation.

14. The method according to claim 12, wherein the core is moved in rotation together with the cutting sleeve.

15. A method for generating an undercut in a bone, comprising:
providing a core with an elongate shaft and with a stamp which is mounted on a distal end of the shaft and which, in a transition area to the shaft, has a run-on bevel ascending in a distal direction, and a cutting sleeve, which is longitudinally movable on the shaft and of which a distal end is formed by at least one segment that can be spread open when pushed onto the run-on bevel and has at least one laterally arranged cutting edge, wherein the at least one segment has a leading edge and a trailing edge in relation to a predefined rotational direction of the cutting sleeve, wherein the leading edge at least partially defines the at least one laterally arranged cutting edge, and wherein the stamp and the shaft of the core have an inner hollow space continuing into a proximal end area of the shaft, and the stamp has at least one lateral aperture;
inserting a distal portion of the core and a distal portion of the cutting sleeve into a bore that has been introduced into the bone; and
rotating the cutting sleeve and moving the cutting sleeve in the distal direction relative to the core in such a way that the at least one segment is spread open over the run-on bevel and the cutting edge of the at least one segment removes bone tissue from a wall of the bore.

16. The method according to claim 15, wherein the core is not moved in rotation.

17. The method according to claim 15, wherein the core is moved in rotation together with the cutting sleeve.

* * * * *